US00PP23825P2

(12) United States Plant Patent
Beekenkamp

(10) Patent No.: US PP23,825 P2
(45) Date of Patent: Aug. 13, 2013

(54) ***BEGONIA* PLANT NAMED 'BKPBEEGL'**

(50) Latin Name: *Begonia hiemalis*
Varietal Denomination: BKPBEEGL

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 92 days.

(21) Appl. No.: 13/200,525

(22) Filed: Sep. 23, 2011

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'BKPBEEGL', characterized by its upright, somewhat outwardly spreading and mounded plant habit; freely basal branching habit; medium-size leaves; uniform and freely flowering habit; and double flowers that are pink in color on both the upper and lower surfaces.

2 Drawing Sheets

Botanical designation: *Begonia hiemalis*.
Cultivar denomination: 'BKPBEEGL'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBEEGL'.

The new *Begonia* plant is a product of a planned breeding program conducted by the Inventor in Amstelveen, The Netherlands. The objective of the breeding program was to develop new freely branching and freely flowering *Begonia* plants with attractive flower color.

The new *Begonia* plant originated from a cross-pollination made by the Inventor in March, 2006 of a proprietary selection of *Begonia hiemalis* identified as code number 06-254-01, not patented, as the female, or seed, parent with a proprietary selection of *Begonia hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in November, 2007.

Asexual reproduction of the new *Begonia* plant by tip cuttings in a controlled greenhouse environment in Amstelveen, The Netherlands since February, 2008 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEGL'.

These characteristics in combination distinguish 'BKPBEEGL' as a new and distinct *Begonia* plant:

1. Upright, somewhat outwardly spreading and mounded plant habit.
2. Freely basal branching habit.
3. Medium-size leaves.
4. Uniform and freely flowering habit.
5. Double flowers that are pink in color on both the upper and lower surfaces.

Plants of the new *Begonia* can be compared to plants of the female parent selection. Plants of the new *Begonia* differ from plants of the female parent selection primarily in flower color as plants of the female parent selection have white-colored flowers with yellow-colored centers.

Plants of the new *Begonia* can be compared to plants of the male parent selection. Plants of the new *Begonia* differ primarily from plants of the male parent selection in the following characteristics:

1. Plants of the new *Begonia* have darker green-colored leaves than plants of the male parent selection.
2. Plants of the new *Begonia* have larger flowers than plants of the male parent selection.
3. Flowers of plants of the new *Begonia* are double types whereas flowers of plants of the male parent selection are single types.

Plants of the new *Begonia* can be compared to plants of the *Begonia* 'Bonbon', not patented. In side-by-side comparisons conducted in Amstelveen, The Netherlands, plants of the new *Begonia* differed from plants of 'Bonbon' in the following characteristics:

1. Plants of the new *Begonia* were more compact than plants of 'Bonbon'.
2. Plants of the new *Begonia* were more uniformly flowering than plants of 'Bonbon'.
3. Plants of the new *Begonia* and 'Bonbon' differed in flower color as plants of 'Bonbon' had brighter and darker pink-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEGL' grown in a container.

The photograph on the second sheet is a close up view of a typical flowers and leaves of 'BKPBEEGL'.

DETAILED BOTANICAL DESCRIPTIONS

Plants used for the aforementioned photographs and following observations and measurements were grown in 12-cm containers during the summer in a glass-covered greenhouse in Maasdijk, The Netherlands. During the production of the plants, day temperatures ranged from 19° C. to 21° C. and night temperatures averaged 19° C. Plants were nine weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEEGL'.

Parentage:

*Female, or seed, parent*.—Proprietary selection of *Begonia hiemalis* identified as code number 06-254-01, not patented.

*Male, or pollen, parent*.—Proprietary selection of *Begonia hiemalis* identified as code number 6500604, not patented.

Propagation:

*Type*.—By tip cuttings.

*Time to initiate roots*.—About 20 days at temperatures of about 25° C.

*Time to produce a rooted young plant*.—About 35 to 36 days at temperatures of about 21° C. to 23° C.

*Root description*.—Medium in thickness, fibrous; white in color; plants of the new Begonia have not been observed to form tubers.

*Rooting habit*.—Moderate branching; medium density.

Plant description:

*Plant form and growth habit*.—Upright, somewhat outwardly spreading and mounded plant habit; plant shape roughly globular to obovate; freely basal branching with about six basal branches per plant with lateral branching; moderately vigorous growth habit.

*Plant height*.—About 22.1 cm.

*Plant width*.—About 27 cm.

*Branch description*.—Length: About 11.3 cm. Diameter: About 7 mm. Internode length: About 3.5 cm. Texture: Sparsely pubescent. Aspect: Upright to about 30° from the vertical. Color, developing: Close to 174A to 174B. Color, fully developed: Close to 178A to 178B.

*Leaf description*.—Arrangement: Alternate, simple. Length: About 9.7 cm. Width: About 8 cm. Shape: Reniform to ovate. Apex: Broadly acute to obtuse. Base: Unequal hastate. Margin: Bi-serrate. Texture, upper and lower surfaces: Smooth, glabrous; velvety. Venation pattern: Palmate; reticulate. Color: Developing leaves, upper surface: Close to 137A to 137B. Developing leaves, lower surface: Close to 148C tinged with close to 177C to 177D. Fully expanded leaves, upper surface: Darker than between 137A and 147A; venation, close to 144A. Fully expanded leaves, lower surface: Close to 147C strongly tinged with close to 183D; venation, close to 146D. Petioles: Length: About 5.5 cm. Diameter: About 4 mm. Texture, upper and lower surfaces: Sparsely pubescent. Color, upper and lower surfaces: Close to 185A.

Flower description:

*Flowering habit*.—Double rotate flowers arranged in axillary cymes; freely flowering habit with about three flowers per cyme and about 54 flowers and flower buds per plant; flowers face upright to outwardly.

*Fragrance*.—None detected.

*Natural flowering season*.—Plants begin flowering about eight weeks after planting; long flowering period, plants flower freely and continuously from spring until autumn in The Netherlands.

*Flower longevity*.—Individual flowers last about ten days on the plant; flowers not persistent.

*Inflorescence height*.—About 14.4 cm.

*Inflorescence diameter*.—About 8.7 cm.

*Flower diameter*.—About 5.7 cm.

*Flower height*.—About 2.4 cm.

*Flower buds*.—Length: About 1.5 cm. Diameter: About 5 mm to 15 mm. Shape: Flattened spherical. Color: Close to 51B.

*Tepals*.—Quantity per flower and arrangement: About two, opposite. Length: About 3.7 cm. Width: About 3.3 cm. Shape: Broadly ovate. Apex: Rounded. Margin: Entire. Texture, upper and lower surfaces: Smooth, glabrous; velvety. Color: When opening, upper surface: Close to 58D; margins, close to 58B to 58C; base tinged with close to 181D. When opening, lower surface: Close to 58D; margins, close to 58C; base tinged with close to 181D. Fully opened, upper and lower surfaces: Close to 58D; margins, close to 58C; base tinged with close to 181D; color does not fade with development.

*Tepaloids*.—Quantity per flower and arrangement: About 20 in multiple whorls. Length: About 2.4 cm to 3.9 cm. Width: About 1 cm to 2.7 cm. Shape: Obovate. Apex: Rounded. Margin: Entire. Texture, upper and lower surfaces: Smooth, glabrous; velvety. Color: When opening, upper and lower surfaces: Close to 62C; margins, close to 62A. Fully opened, upper and lower surfaces: Close to 62C; margins, close to 62A; color does not fade with development.

*Peduncles*.—Angle: About 30° from vertical. Strength: Moderately strong. Length: About 7.6 cm. Diameter: About 4 mm. Texture: Smooth, glabrous. Color: Close to 174A to 174B.

*Pedicels*.—Angle: About 20° from the peduncle. Strength: Moderately strong. Length: About 2.5 cm. Diameter: About 2 mm. Texture: Smooth, glabrous. Color: Close to 174B.

*Reproductive organs*.—Reproductive organ development has not been observed on plants of the new *Begonia*.

*Seeds and fruits*.—Seed and fruit development production has not been observed on plants of the new *Begonia*.

Disease/pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEEGL' as illustrated and described.

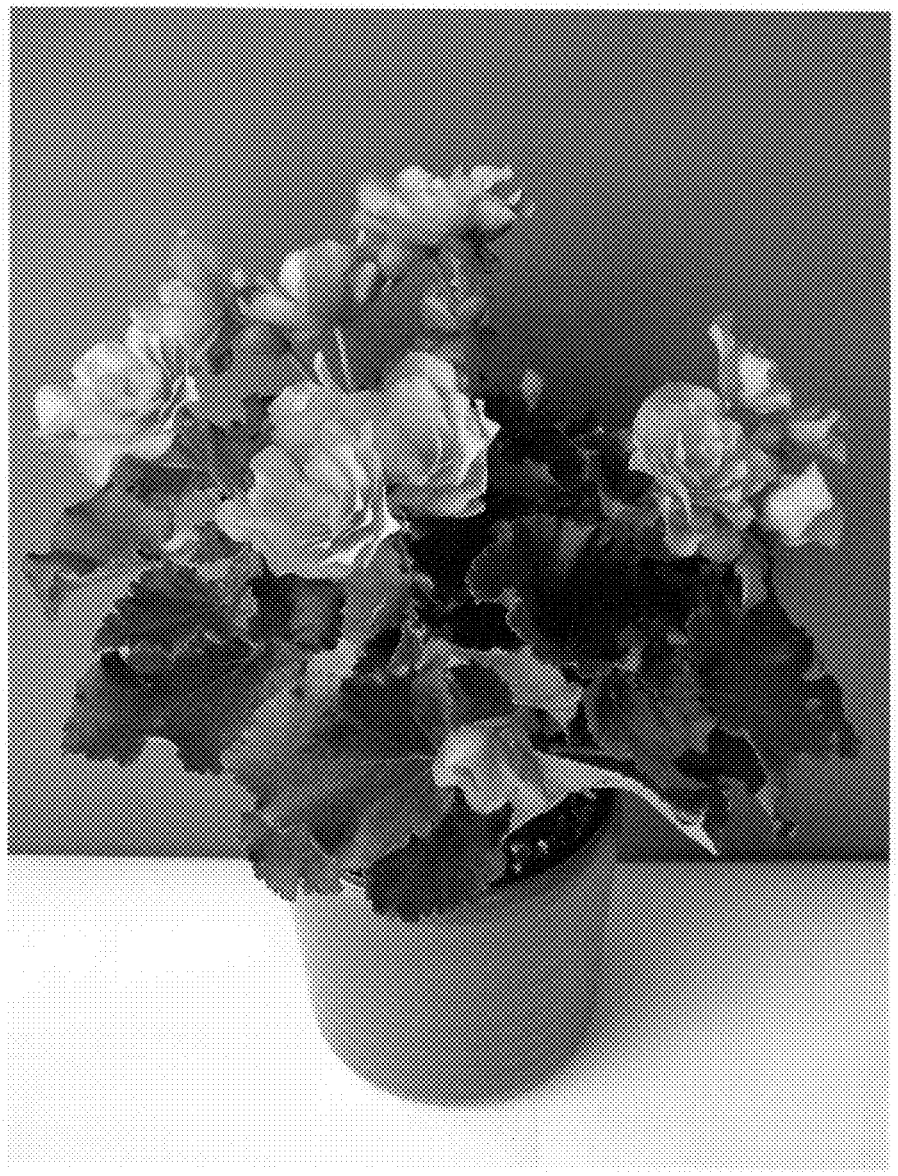

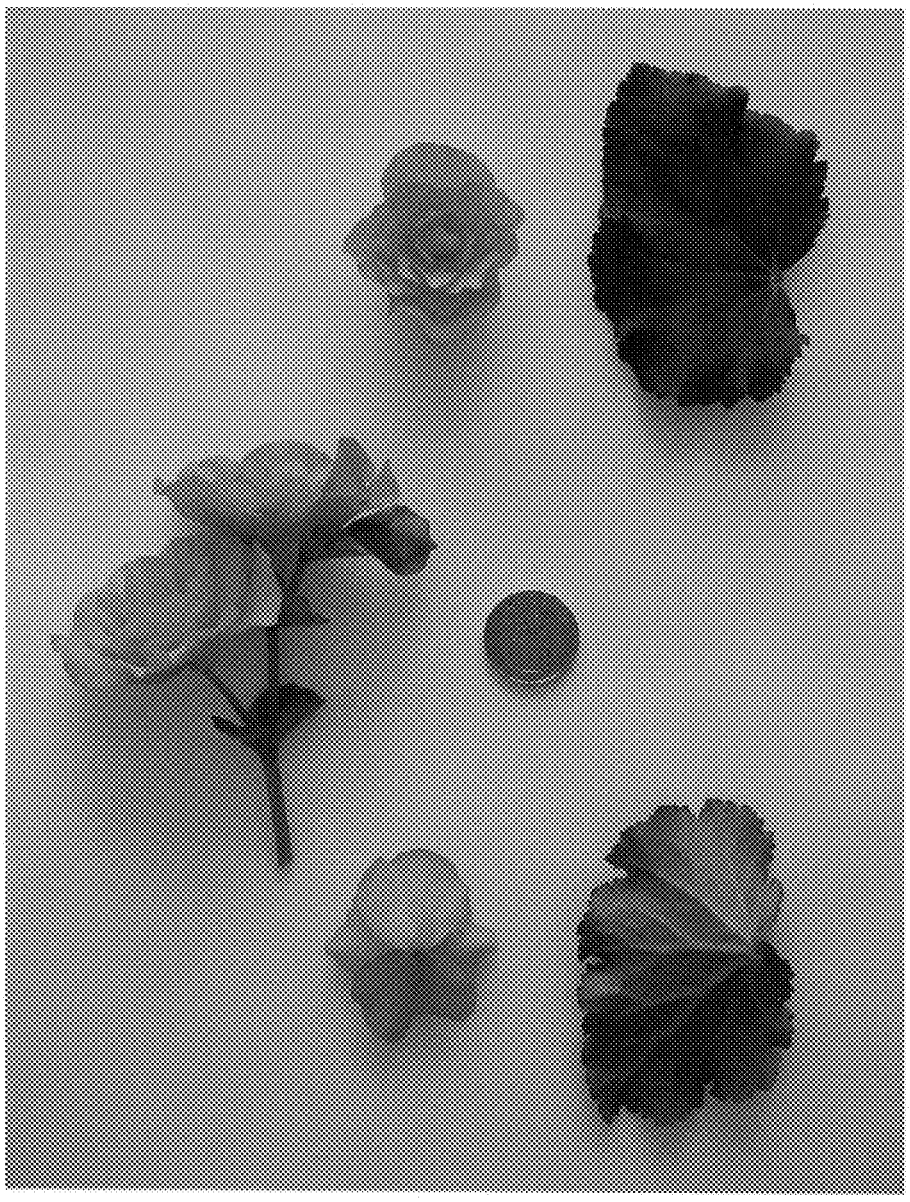

* * * * *